US008148344B2

(12) United States Patent
Akinc et al.

(10) Patent No.: US 8,148,344 B2
(45) Date of Patent: Apr. 3, 2012

(54) COMPOSITIONS AND METHODS FOR MEDIATING RNAI IN VIVO

(75) Inventors: Akin Akinc, Needham, MA (US); Tomoko Nakayama, Cambridge, MA (US); David Konys, Natick, MA (US); Markus Stoffel, Zurich (CH); Christian Wolfrum, Zurich (CH)

(73) Assignees: Alnylam Pharmaceuticals, Inc., Cambridge, MA (US); ETH Zurich, Zurich (CH)

( * ) Notice: Subject to any disclaimer, the term of this patent is extended or adjusted under 35 U.S.C. 154(b) by 62 days.

(21) Appl. No.: 12/412,206

(22) Filed: Mar. 26, 2009

(65) Prior Publication Data
US 2010/0003317 A1    Jan. 7, 2010

Related U.S. Application Data

(60) Provisional application No. 61/040,386, filed on Mar. 28, 2008.

(30) Foreign Application Priority Data

Mar. 27, 2008 (EP) .................................... 08005800

(51) Int. Cl.
*A61K 31/70* (2006.01)
*C07H 21/02* (2006.01)
*C07H 21/04* (2006.01)
*C12Q 1/68* (2006.01)

(52) U.S. Cl. .................... 514/44 A; 536/23.1; 536/24.1; 536/24.5; 435/375; 435/377

(58) Field of Classification Search ............. 435/6, 91.1, 435/91.31, 455; 536/23.1, 24.5
See application file for complete search history.

(56) References Cited

U.S. PATENT DOCUMENTS

| | | |
|---|---|---|
| 4,426,330 A | 1/1984 | Sears |
| 4,534,899 A | 8/1985 | Sears |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 5,013,556 A | 5/1991 | Woodle et al. |
| 5,032,401 A | 7/1991 | Jamas et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,138,045 A | 8/1992 | Cook et al. |
| 5,213,804 A | 5/1993 | Martin et al. |
| 5,214,136 A | 5/1993 | Lin et al. |
| 5,218,105 A | 6/1993 | Cook et al. |
| 5,225,212 A | 7/1993 | Martin et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,272,250 A | 12/1993 | Spielvogel et al. |
| 5,292,873 A | 3/1994 | Rokita et al. |
| 5,317,098 A | 5/1994 | Shizuya et al. |
| 5,356,633 A | 10/1994 | Woodle et al. |
| 5,371,241 A | 12/1994 | Brush |
| 5,391,723 A | 2/1995 | Priest |
| 5,414,077 A | 5/1995 | Lin et al. |
| 5,416,203 A | 5/1995 | Letsinger |
| 5,451,463 A | 9/1995 | Nelson et al. |
| 5,486,603 A | 1/1996 | Buhr |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,525,465 A | 6/1996 | Haralambidis et al. |
| 5,540,935 A | 7/1996 | Miyazaki et al. |
| 5,541,313 A | 7/1996 | Ruth |
| 5,545,730 A | 8/1996 | Urdea et al. |
| 5,552,538 A | 9/1996 | Urdea et al. |
| 5,556,948 A | 9/1996 | Tagawa et al. |
| 5,565,552 A | 10/1996 | Magda et al. |

(Continued)

FOREIGN PATENT DOCUMENTS

EP    0445131 B1    4/1994

(Continued)

OTHER PUBLICATIONS

Augustus Ayanna S et al: "Routes of FA delivery to cardiac muscle: Modulation of lipoprotein lipolysis alters uptake of TG-derived FA." American Journal of Physiology, Feb. 2003, pp. E331-E339, vol. 284, No. 2, Part 1. Affleck D G et al: "Augmentation of myocardial transfection using TerplexDNA: a novel gene delivery system." Gene Therapy Mar. 2001, vol. 8, No. 5, pp. 349-353.
Bichenkov E E et al: "Interaction of Cholesterol-Modified Polynucleotide With Phosphatidylcholine Liposomes" Biologicheskie Membrany (Moscow), 1988, pp. 735-742, vol. 5, No. 7.
Elbashir S M et al: "Functional anatomy of siRNAs for mediating efficient RNAi in *Drosophila melanogaster* embryo lysate" EMBO Journal, Oxford University Press, Surrey, GB, Dec. 3, 2001, pp. 6877-6888, vol. 20, No. 23.
Granot E et al: "Core modification of human low-density lipoprotein by artificial triacylglycerol emulsion" Biochimica Et Biophysica Acta—Lipids and Lipid Metabolism 1985 NL, 1985, pp. 308-315, vol. 833, No. 2.

(Continued)

*Primary Examiner* — Sean McGarry
(74) *Attorney, Agent, or Firm* — Fenwick & West LLP

(57) ABSTRACT

This invention relates to new formulated lipid particles (FLiPs) comprising at least one of a single or double stranded oligonucleotide, where the oligonucleotide has been conjugated to a lipophile and at least one of an emulsion or liposome to which the conjugated oligonucleotide has been aggregated, admixed or associated. These particles have surprisingly been shown to effectively deliver oligonucleotides to heart, lung and muscle where they effect gene silencing.

25 Claims, 7 Drawing Sheets

U.S. PATENT DOCUMENTS

| | | | |
|---|---|---|---|
| 5,567,810 | A | 10/1996 | Weis et al. |
| 5,574,142 | A | 11/1996 | Meyer, Jr. et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,371 | A | 12/1996 | Sessler et al. |
| 5,591,584 | A | 1/1997 | Chang et al. |
| 5,595,726 | A | 1/1997 | Magda et al. |
| 5,597,696 | A | 1/1997 | Linn et al. |
| 5,599,923 | A | 2/1997 | Sessler et al. |
| 5,599,928 | A | 2/1997 | Hemmi et al. |
| 5,607,677 | A | 3/1997 | Jamas et al. |
| 5,608,046 | A | 3/1997 | Cook et al. |
| 5,688,941 | A | 11/1997 | Cook et al. |
| 6,747,014 | B2 | 6/2004 | Teng et al. |
| 6,887,906 | B1 | 5/2005 | Teng et al. |
| 2003/0027780 | A1 | 2/2003 | Hardee |
| 2003/0143732 | A1 | 7/2003 | Fosnaugh et al. |
| 2004/0229831 | A1 | 11/2004 | Teng |
| 2004/0259247 | A1 | 12/2004 | Tuschl et al. |
| 2005/0281781 | A1 | 12/2005 | Ostroff |
| 2006/0270623 | A1* | 11/2006 | McSwiggen ............... 514/44 |
| 2007/0004664 | A1 | 1/2007 | McSwiggen et al. |
| 2007/0031844 | A1 | 2/2007 | Khvorova et al. |
| 2007/0249551 | A1 | 10/2007 | Teng |
| 2009/0239934 | A1* | 9/2009 | Schmitt-Milas et al. ... 514/44 A |

FOREIGN PATENT DOCUMENTS

| | | |
|---|---|---|
| EP | 0496813 B1 | 12/1994 |
| EP | 2105145 A1 | 9/2009 |
| WO | WO 90/04384 | 5/1990 |
| WO | WO 90/10448 A | 9/1990 |
| WO | WO 91/05545 | 5/1991 |
| WO | WO 94/20073 | 9/1994 |
| WO | WO 96/10391 | 4/1996 |
| WO | WO 99/01579 | 1/1999 |
| WO | WO 00/50050 | 8/2000 |
| WO | WO 01/48233 A | 7/2001 |
| WO | WO 02/087594 A | 11/2002 |
| WO | WO 03/011252 A | 2/2003 |
| WO | WO 2004/065601 | 8/2004 |
| WO | WO 2005/118612 A | 12/2005 |
| WO | WO 2007/112753 A | 10/2007 |

OTHER PUBLICATIONS

Hamidi Mehrdod et al: "Lipoproteins: From physiological roles to drug delivery potentials" Critical Reviews in Therapeutic Drug Carrier Systems, Jan. 1, 2006, pp. 497-523, vol. 23, No. 6.

Hara T et al: "In vivo gene delivery to the liver using reconstituted chylomicron remnants as a novel nonviral vector" Proceedings of the National Academy of Sciences of USA, National Academy of Science, Washington, DC, Dec. 23, 1997, pp. 14547-14552, vol. 94, No. 26.

Kim J-S E1 Al: "A new non-viral DNA delivery vector: the terplex system" Journal of Controlled Release, Elsevier, Amsterdam, NL, Apr. 30, 1998, pp. 175-182, vol. 53, No. 1-3.

Lutz O et al: "Fat emulsion particle size: Influence on the clearance rate and the tissue lipolytic activity" American Journal of Clinical Nutrition1989 US, 1989, pp. 1370-1381, vol. 50, No. 6.

Yu L et al: "TerplexDNA gene carrier system targeting artery wall cells" Journal of Controlled Release, Elsevier, Amsterdam, NL, May 14, 2001, pp. 179-189, vol. 72, No. 1-3.

Wolfrum Christian et al: "Mechanisms and optimization of in vivo delivery of lipophilic siRNAs." Nature Biotechnology Oct. 2007, pp. 1149-1157, vol. 25, No. 10.

PCT International Search Report and Written Opinion, PCT/US2009/038437, Oct. 23, 2009, 21 Pages.

Allen, T.M., et al., "Large unilamellar liposomes with low uptake into the reticuloendothelial system," FEBS Letters, Oct. 1987, vol. 223, No. 1, pp. 42-46.

Blume, G., et al., "Liposomes for the sustained drug release in vivo," Biochimica et Biophysica Acta, 1990, vol. 1029, pp. 91-97.

Constantinides, P., et al., "Formulation and Intestinal Absorption Enhancement Evaluation of Water-in-Oil Microemulsions Incorporating Medium-Chain Glycerides," Pharmaceutical Research, 1994, vol. 11, No. 10, 1385-1390.

Crooke S., et al., "Pharmacokinetic Properties of Several Novel Oligonucleotide Analogs in mice," J. Pharmacol. Exp. Ther., 1996, vol. 277, No. 2, pp. 923-937.

Du Plessis, J., et al., "Research Articles Topical delivery of liposomally encapsulated gamma-interferon," Antiviral Research, 1992, vol. 18, pp. 259-265.

Higuchi et al., in Remington's Pharmaceutical Sciences, "Particle Phenomena and Coarse Dispersions," Chapter 21, Mack Publishing Co., Easton, Pa., 1985, p. 301-329.

Ho, H., et al., "Preparation of Microemulsions Using Polyglycerol Fatty Acid Esters as Surfactant for the Delivery of Protein Drugs," J. Pharm. Sci., Feb. 1996, vol. 85, No. 2, pp. 138-143.

Hu, Z., et al., "Topical delivery of cyclosporin A from non-ionic liposomal systems: an in vivo/in vitro correlation study using hairless mouse skin," S.T.P.Pharma. Sci., 1994, vol. 4, No. 6, pp. 466-469.

Illum, L., et al., "The organ uptake of intravenously administered colloidal particles can be altered using a non-ionic surfactant (Poloxamer 338)," FEBS Lett., Feb. 1984, vol. 167, No. 1, pp. 79-82.

Kabanov, A., et al., "A new class of antivirals: antisense oligonucleotides combined with a hydrophobic substituent effectively inhibit influenza virus reproduction and synthesis of virus-specific proteins in MDCK cells," FEBS Lett., 1990, vol. 259, No. 2, pp. 327-330.

Klibanov, A., et al., "Amphipathic polyethyleneglycols effectively prolong the circulation time of liposomes," FEBS Lett., Jul. 1990, vol. 268, No. 1, pp. 235-237.

Lee, V., et al., "Mucosal Penetration Enhancers for Facilitation of Peptide and Protein Drug Absorption," Critical Reviews in Therapeutic Drug Carrier Systems, 1991, vol. 8, No. 2, pp. 91-192.

Leung, R., et al., "Controlled Release of Drugs: Polymers and Aggregate Systems," Chapter 6, Microemulsions: An Evolving Technology for Pharmaceutical Applications, Rosoff, M., Ed., 1989, VCH Publishers, New York, pp. 185-215.

Letsinger, R., et al., "Cholesteryl-conjugated oligonucleoptides: Sythesis, properties, and activity as inhibitors of replication of human immunodeficiency virus in cell culture," Proc. Natl. Acid. Sci. USA, Sep. 1989, vol. 86, pp. 6553-6556.

Mishra, R., et al., "Improved leishmanicidal effect of phosphorotioate antisense oligonucleotides by LDL-mediated delivery," Biochim. Biophys. Acta, 1995, vol. 1264, pp. 229-237.

Miyao, T., et al., "Stability and Pharmacokinetic Characteristics of Oligonucleotides Modified at Terminal Linkages in Mice," Antisense Research and Dev., 1995, vol. 5, pp. 115-121.

Manoharan, M., et al., "Cholic Acid-Oligonucleotide Conjugages for Antisense Applications," Biorg. Med. Chem. Let., 1994, vol. 4, No. 8, pp. 1053-1060.

Manoharan, M., et al., "Oligonucleotide Conjugates: Alteration of the Pharmacokinetic Properties of Antisense Agents," Nucleosides & Nucleotides, 1995, vol. 14, Nos. 3-5, pp. 969-973.

Manoharan, M., et al., "Lipidic Nucleic Acids," Tetrahedron Lett., 1995, vol. 36, No. 21, pp. 3651-3654.

Manoharan, M., et al., "Introduction of a Lipophilic Thioether Tether in the Minor Groove of Nucleic Acids of Antisense Applications," Biorg. Med. Chem. Let., 1993, vol. 3, No. 12, pp. 2765-2770.

Manoharan M., et al., "Chemical Modifications to Improve Uptake and Bioavailability of Anisense Oligonucleotides", Annals of the New York Academy of Sciences, 1992, vol. 660, pp. 306-309.

Oberhauser, B., et al., "Effective incorporation of 2'-O-methyloligoribonucleotides into liposomes and enchanced cell associate through modification with thiocholesterol," Nucl. Acids Res., 1992, vol. 20, No. 3, pp. 533-538.

Ritschel, W.A., "Microemulsions for Improved Peptide Absorption from the Gastointestinal Tract," Meth. Find. Exp. Clin. Pharmacol., 1993, vol. 13, No. 3, pp. 205-220.

Saison-Behmoaras, T., et al., "Short modified antisense oligonucleotides directed against Ha-ras point mutation induce selective cleavage of the mRNA and inhibit T24 cells proliferation," EMBO J, 1991, vol. 10, pp. 1111-1118.

Shea, R., et al., "Synthesis, hybridization properties and antiviral activity of lipid-oligodeoxynucleotide conjugates," Nucl. Acids Res., 1990, vol. 18, No. 13, pp. 3777-3783.

Svinarchuk, FP., et al., "Inhibition of HIV proliferation in MT-4 cells by antisense oligonucleotide conjugated to lipophilic groups," Biochimie, 1993, vol. 75, p. 49-54.

Sunamoto, J., et al., "Liposomal Membranes. V. Interaction of Zinc (II) Ion with Egg Phosphatidylcholine Liposomes," Bull. Chem. Soc. Jpn., 1980, vol. 53, No. 10, pp. 2778-2781.

Soutschek, J., et al., "Therapeutic silencing of an endogenous gene by systemic administration of modified siRNAs," Nature, Nov. 2004, vol. 432, pp. 173-178.

Takakura, Y., et al., "Uptake Characteristics of Oligonucleotides in the Isolated Rat Liver Perfusion System," Antisense & Nucl. Acid Drug Dev., 1996, vol. 6, pp. 177-183.

Torchilin, V. P., "Recent advances with liposomes as pharmaceutical carriers," Nature Rev. Drug Discov., Feb. 2005, vol. 4, No. 2, pp. 145-160.

Weiner, N., et al., "Liposomes: A Novel Topical Delivery System for Pharmaceutical and Cosmetic Applications," Journal of Drug Targeting, 1992, vol. 2, pp. 405-410.

Wolfrum, et al., "Mechanisms and optimization of in vivo delivery of lipophilic siRNAs," Nature Biotechnology, Oct. 2007, vol. 25, No. 10, pp. 1149-1157.

Wu, N., et al., "Increased Microvascular Permeability Contributes to Preferential Accumulation of Stealth Liposomes in Tumor Tissue," Cancer Research, Aug. 15, 1993, vol. 53, pp. 3765-3770.

Idson, B.,., "Pharmaceutical Emulsions," Pharmaceutical Dosage Forms, Chapter 6, Lieberman, Rieger and Banker (Eds.), 1988, Marcel Dekker, Inc., New York, N.Y., vol. 1, p. 199-243.

Rosoff, M., "Specialized Pharmaceutical Emulsions," Pharmaceutical Dosage Forms, Chapter 7, Lieberman, Rieger and Banker (Eds.), 1988, Marcel Dekker, Inc., New York, N.Y., vol. 1, p. 245-283.

Block, L., "Emulsions and Microemulsions," Pharmaceutical Dosage Forms, Chapter 9, Lieberman, Rieger and Banker (Eds.), 1988, Marcel Dekker, Inc., New York, N.Y., vol. 2, p. 335-378.

Agrawal, S., et al., "Antisense oligonucleotides: towards clinical trials." Trends in Biotechnology. Oct. 1996, vol. 14, pp. 376-387.

Bass, B., "The short answer," Nature, May 24, 2001, pp. 428-429, vol. 411.

Elbashir, S., et al., "Analysis of gene function in somatic mammalian cells using small interfering RNAs," Methods, 2002, pp. 199-213, vol. 26.

Elbashir, S., et al., "Duplexes of 21-nucleotide RNAs mediate RNA interference in mammalian cell culture," Nature, May 24, 2001, p. 494-498, vol. 411.

Elbashir, S., et al., "Functional Anatomy of siRNAs for Mediating Efficient RNAi in Drosophila melanogaster Embryo Lysate", The EMBO Journal, 2001, pp. 6877-6888, vol. 20, No. 23.

Elbashir, S., et al., "RNA Interference is Mediated by 21-and 22 Nucleotide RNAs," Genes & Development, 2001, pp. 188-200, vol. 15.

Fire, A., "RNA-triggered Gene Silencing," Trends in Genetics, Sep. 1999, pp. 358-363, vol. 15, No. 9.

Fire, A., et al., "Potent and Specific Genetic Interference by Double Stranded RNA in Caenorhabditis elegans," Nature, Feb. 19, 1998, pp. 806-811, vol. 391.

Tuschl, T., "Functional genomics: RNA sets the standard," Nature, Jan. 16, 2003, vol. 421, No. 6920, pp. 220-221.

Tuschl T., "RNA Interference and Small Interfering RNAs" Chembiochem, 2001, pp. 239-245, vol. 2.

Tuschl, T., et al., "Small Interfering RNAs: A Revolutionary Tool for the Analysis of Gene Function and Gene Therapy," Molecular Interventions, 2002, pp. 158-167, vol. 2, No. 3.

Tuschl, T., "Mammalian RNA Interference," RNAi, A Guide to Gene Silencing, Chapter 13, G.J. Hannon (ed,), 2003, pp. 265-295.

Tuschl, T., et al., "Targeted mRNA Degradation by Double-Stranded RNA in Vitro," Genes & Development, 1999, pp. 3191-3197, vol. 13.

Tuschl, T., "Expanding small RNA interference," Nature Biotechnology, May 2002, pp. 446-448, vol. 20.

Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.

* cited by examiner

COMPOSITIONS AND METHODS FOR MEDIATING RNAI IN VIVO

RELATED APPLICATIONS

This application claims the benefit of European application no. 08005800.1, filed Mar. 27, 2008, and U.S. Provisional Application No. 61/040,386, filed Mar. 28, 2008. The entire contents of these priority applications are incorporated herein by reference.

FIELD OF THE INVENTION

This invention relates to compositions containing oligonucleotides, both single and double stranded, and their use in mediating RNA interference. More specifically, the present invention relates to certain formulations for oligonucleotides which enable tissue-specific delivery and reduction of target expression by the formulated oligonucleotides.

BACKGROUND OF THE INVENTION

Double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant or unwanted regulation of a gene.

Despite significant advances in the field of RNAi and advances in the treatment of pathological processes, there remains a need for formulations that can selectively and efficiently deliver agents to cells where silencing can then occur.

While delivery of oligonucleotides across plasma membranes in vivo has been achieved using vector-based delivery systems, high-pressure intravenous injections of oligonucleotides and various chemically-modified oligonucleotides, including cholesterol-conjugated, lipid encapsulated and antibody-mediated oligonucleotides, to date, delivery remains the largest obstacle for in vivo oligonucleotide therapeutics.

SUMMARY OF THE INVENTION

The invention provides compositions containing oligonucleotides, either single-stranded or double-stranded, and methods for inhibiting the expression of a gene in a cell or mammal using such oligonucleotides in combination with a lipid formulation. The invention also provides compositions and methods for treating pathological conditions and diseases caused by the expression of a target gene, such as cancer. Double stranded oligonucleotides featured herein include double-stranded RNA (dsRNA) having an RNA strand (the antisense strand) having a region which is less than 30 nucleotides in length, generally 19-24 nucleotides in length, and is substantially complementary to at least part of an mRNA transcript of the target gene. In one embodiment, a dsRNA for inhibiting expression of the target gene includes at least two sequences that are complementary to each other. The dsRNA includes a sense strand having a first sequence and an antisense strand having a second sequence. The antisense strand includes a nucleotide sequence that is substantially complementary to at least part of an mRNA encoding a target gene, and the region of complementarity is less than 30 nucleotides in length, and at least 15 nucleotides in length. Generally, the dsRNA is 19 to 24, e.g., 19 to 21 nucleotides in length. In some embodiments the dsRNA strands are independently about 10 to about 15 nucleotides in length, and in other embodiments the are from about 25 to about 30 nucleotides in length.

The single-stranded oligonucleotides suitable for use in the featured compositions also include a nucleotide sequence that is substantially complementary to at least part of an mRNA encoding a target gene, and the region of complementarity is less than 30 nucleotides in length, and at least 15 nucleotides in length. Generally, the single stranded oligonucleotides are 19 to 24, e.g., 19 to 21 nucleotides in length. In one embodiment the strand is 25-30 nucleotides. In some embodiments, the single-stranded oligonucleotide has less than 100% complementarity to the target mRNA, RNA or DNA.

The oligonucleotides featured herein can include naturally occurring nucleotides or can include at least one modified nucleotide, such as a 2'-O-methyl modified nucleotide, a nucleotide having a 5'-phosphorothioate group, and a terminal nucleotide linked to a conjugate group, such as a cholesteryl derivative or vitamin E group. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

The oligonucleotides featured herein can be stabilized by one or more modifications to avoid degradation of the oligonucleotides. Typical modifications include phosphorothioate DNA units, 2'-O-methyl RNA units, 2'-O-methoxy-ethyl RNA units, peptide nucleic acid units, N3'-P5' phosphoroamidate DNA units, 2' fluoro-ribo nucleic acid units, Locked nucleic acid units, morpholino phosphoroamidate nucleic acid units, cyclohexane nucleic acid units, tricyclonucleic acid units, 2'-O-alkylated nucleotide modifications, 2'-Deozy-2'-fluoro modifications, 2,4-difluorotoluoyl modifications, 4'-thio ribose modifications, or boranophospate modifications.

In one embodiment, an oligonucleotide is incorporated in "formulated lipid particle" (FLiP). It has been surprisingly discovered that when oligonucleotides, either single- or double stranded, are formulated into FLiPs, both delivery and silencing are effected in tissues in vivo, particularly heart, lung and muscle tissues.

A FLiP includes (a) at least one of a single or double stranded oligonucleotide, where the oligonucleotide has been conjugated to a lipophile, and (b) at least one of an emulsion or liposome to which the conjugated oligonucleotide has been aggregated, admixed or associated.

In one aspect, the invention provides a pharmaceutical composition for inhibiting the expression of the target gene in an organism, generally a human subject. The composition typically includes one or more of the oligonucleotides, e.g., dsRNAs, described herein and a pharmaceutically acceptable carrier or delivery vehicle. In one embodiment, the composition is used for treating a disease or disorder affecting the heart, lung or other muscle tissue.

In another aspect, the invention provides a method for delivering an oligonucleotide to a specific tissue, such as heart or lung tissue, and inhibiting the expression of the target gene in a cell of the tissue, e.g., a muscle cell, by performing the following steps:

(a) introducing into an organism or tissue of an organism a FLiP, and wherein the oligonucleotide of the FLiP, upon contact with a cell expressing the target gene, inhibits expression of the target gene; and (c) maintaining the cell in step (a) for a time sufficient to obtain degradation of the mRNA transcript of the target gene, thereby inhibiting expression of the target gene in the cell.

In another aspect, the invention provides methods for treating, preventing or managing pathological processes mediated by a target gene by administering to a patient in need of such treatment, prevention or management, a therapeutically or prophylactically effective amount of one or more of the FLiPs featured.

In yet another aspect, the invention provides a method for delivering oligonucleotides into muscle in vivo and for the treatment of muscle diseases. Muscle tissue, as used herein, refers to skeletal, cardiac, smooth and any cell type exhibiting the characteristics of muscle lineage.

In one aspect, the invention relates to a liposome having triacylglycerol, one or more phospholipids, glycerol, and one or several lipid-binding proteins aggregated via a lipophilic linker molecule with a single- or double-stranded oligonucleotide, where the liposome has an affinity for muscle tissue, such as heart and/or lung tissue.

The following detailed description discloses how to make and use the compositions and FLiPs containing oligonucleotides to inhibit the expression of the target gene and any of one or more additional genes, respectively, as well as compositions and methods for treating diseases and disorders caused by the expression of these genes.

DETAILED DESCRIPTION OF THE INVENTION

Figure 1:
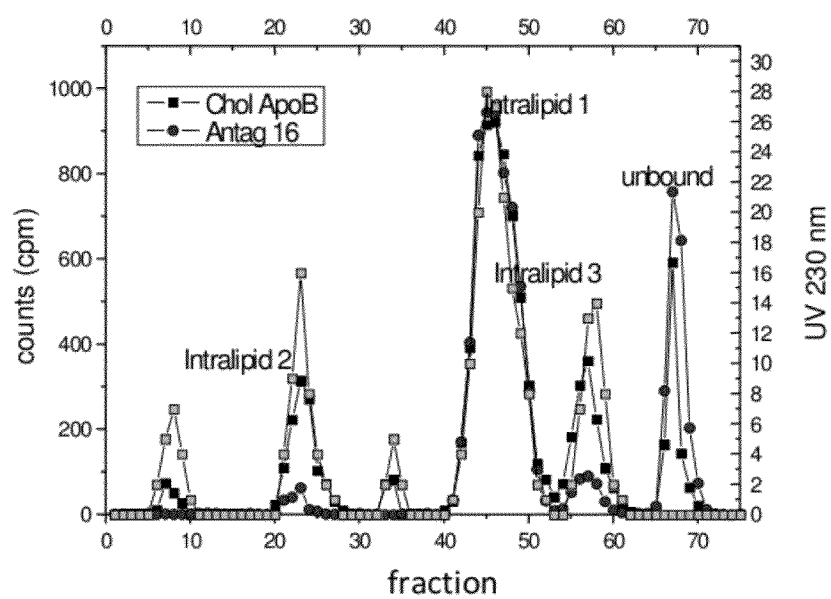
FIG. 1 is an analysis of Intralipid® by FPLC. Cholesterol-conjugated RNAs (Chol-apoB1-siRNA and antagomir-16) bound to Intralipid® peak#1. Light squares indicate Intralipid® fractions.

The invention provides compositions and methods for inhibiting the expression of a target gene in a cell or mammal using single- and/or double-stranded oligonucleotides. The oligonucleotides are conjugated to one or more lipophiles and packaged and or formulated into what is referred to herein as a "formulated lipid particle" (FLiP). It has been surprisingly discovered that when lipophilic conjugated oligonucleotides, either single- or double stranded, are formulated as FLiPs, both delivery and silencing are effected in tissues in vivo, particularly heart, lung and muscle tissues.

A FLiP includes (a) at least one of a single or double stranded oligonucleotide, where the oligonucleotide has been conjugated to a lipophile, and (b) at least one of an emulsion or liposome to which the conjugated oligonucleotide has been aggregated, admixed or associated.

The invention also provides compositions and methods for treating pathological conditions and diseases, such as diseases and disorders associated with muscle tissue, in a mammal caused by the overexpression of the target gene. The oligonucleotide component, whether single stranded or double stranded, directs the sequence-specific degradation of mRNA through the antisense mechanism known as RNA interference (RNAi).

The oligonucleotides of the featured compositions include dsRNAs, which include an RNA strand (the antisense strand) having a region which is less than 30 nucleotides in length, generally 19-24 nucleotides in length, specifically 21-23 nucleotides in length, and which is substantially complementary to at least part of an mRNA transcript of the target gene. In one embodiment the oligonucleotides are specifically between 25-30 nucleotides in length, encompassing those of 25, 26, 27, 28, 29 or 30 nucleotides. The use of these dsRNAs enables the targeted degradation of mRNAs of genes that are implicated in replication and or maintenance of disease states, e.g. cancer, in mammals. Very low dosages of formulated dsRNAs as FLiPs in particular can specifically and efficiently mediate RNAi, resulting in significant inhibition of expression of the target gene. The methods and compositions featured herein contain formulated dsRNAs that are useful for treating pathological processes mediated by target gene expression, such as those of the lung, heart, and other muscle tissues.

The FLiP pharmaceutical compositions featured in the invention include a dsRNA having an antisense strand comprising a region of complementarity which is less than 30 nucleotides in length, generally 19-24 nucleotides in length, and is substantially complementary to at least part of an RNA transcript of the target gene, optionally with a pharmaceutically acceptable carrier.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced by a nucleotide containing, for example, inosine. In another example, adenine and cytosine anywhere in the oligonucleotide can be replaced with guanine and uracil, respectively to form G-U Wobble base pairing with the target mRNA.

As used herein, "target sequence" refers to a contiguous portion of the nucleotide sequence of an mRNA molecule formed during the transcription of the target gene, including mRNA that is a product of RNA processing of a primary transcription product. Target sequences may further include RNA precursors, either pri or pre-microRNA, or DNA which encodes the mRNA.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA having one oligonucleotide strand 21 nucleotides in length and another oligonucleotide strand 23 nucleotides in length, wherein the longer oligonucleotide comprises a sequence of 21 nucleotides that is fully complementary to the shorter oligonucleotide, may yet be referred to as "fully complementary."

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., encoding target gene). For example, a polynucleotide is complementary to at least a part of a target gene mRNA if the sequence is substantially complementary to a non-interrupted portion of a mRNA encoding target gene.

As used herein the term "oligonucleotide" embraces both single and double stranded polynucleotides.

The term "double-stranded RNA" or "dsRNA", as used herein, refers to a complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop." Where the two strands are connected covalently by means other than an uninterrupted chain of nucleotides between the 3'-end of one strand and the 5' end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

"Introducing into a cell," when referring to an oligonucleotide, means facilitating uptake or absorption into the cell, as is understood by those skilled in the art. Absorption or uptake of oligonucleotides can occur through unaided diffusive or active cellular processes, or by auxiliary agents or devices. The meaning of this term is not limited to cells in vitro; an oligonucleotide may also be "introduced into a cell," wherein the cell is part of a living organism. In such instance, introduction into the cell will include the delivery to the organism. For example, for in vivo delivery, oligonucleotides can be injected into a tissue site or administered systemically. In vivo delivery can also be by a beta-glucan delivery system, such as those described in U.S. Pat. Nos. 5,032,401 and 5,607,677, and U.S. Publication No. 2005/0281781. U.S. Pat. Nos. 5,032,401 and 5,607,677, and U.S. Publication No. 2005/0281781 are hereby incorporated by reference in their entirety. In vitro introduction into a cell includes methods known in the art such as electroporation and lipofection.

The terms "silence," "inhibit the expression of," "down-regulate the expression of," "suppress the expression of," and the like, in as far as they refer to target gene, herein refer to the at least partial suppression of the expression of the target gene, as manifested by a reduction of the amount of target mRNA, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to the target gene expression, e.g. the amount of protein encoded by the target gene which is secreted by a cell, or the number of cells displaying a certain phenotype, e.g., apoptosis. In principle, gene silencing may be determined in any cell expressing the target, either constitutively or by genomic engineering, and by any appropriate assay. However, when a reference is needed in order to determine whether a given oligonucleotide inhibits the expression of the gene by a certain degree, and therefore is encompassed by the instant invention, the assays provided in the Examples below shall serve as such reference.

For example, in certain instances, expression of the gene is suppressed by at least about 20%, 25%, 30%, 35%, 40%, 45%, or 50% by administration of compositions having single- or double-stranded oligonucleotides formulated as FLiPs. In some embodiments, the target gene is suppressed by at least about 60%, 70%, or 80% by administration of the compositions having oligonucleotides formulated as FLiPs. In other embodiments, the target gene is suppressed by at least about 85%, 90%, or 95% by of the compositions having oligonucleotides formulated as FLiPs.

As used herein in the context of gene expression, the terms "treat," "treatment," and the like, refer to relief from or alleviation of pathological processes mediated by target gene expression. Insofar as they relate to any of the other conditions recited herein below (other than pathological processes mediated by target gene expression), the terms "treat," "treatment," and the like mean to relieve or alleviate at least one symptom associated with such condition, or to slow or reverse the progression of such condition, such as the slowing and progression of a disease or disorder of the heart or lung or muscle tissue, such as myocarditis or a myopathy.

As used herein, the phrases "therapeutically effective amount" and "prophylactically effective amount" refer to an amount that provides a therapeutic benefit in the treatment, prevention, or management of pathological processes mediated by target gene expression or an overt symptom of pathological processes mediated by target gene expression. The specific amount that is therapeutically effective can be readily determined by ordinary medical practitioner, and may vary depending on factors known in the art, such as, e.g. the type of pathological processes mediated by target gene expression, the patient's history and age, the stage of pathological processes mediated by target gene expression, and the administration of other anti-pathological processes mediated by target gene expression agents.

As used herein, a "pharmaceutical composition" comprises a pharmacologically effective amount of an oligonucleotide formulated as a FLiP and optionally a pharmaceutically acceptable carrier. As used herein, "pharmacologically effective amount," "therapeutically effective amount" or simply "effective amount" refers to that amount of an oligonucleotide or as when formulated as a FLiP effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. Oligonucleotides

IIa. Double-Stranded Oligonucleotides

In one embodiment, the invention provides double-stranded ribonucleic acid (dsRNA) molecules for inhibiting the expression of the target gene (alone or in combination with a second dsRNA for inhibiting the expression of a second target gene) in a cell or mammal, wherein the dsRNA comprises an antisense strand comprising a region of complementarity which is complementary to at least a part of an mRNA formed in the expression of the target gene, and wherein the region of complementarity is less than 30 nucleotides in length, generally 19-24 nucleotides in length, and wherein the dsRNA, upon contact with a cell expressing the target gene, inhibits the expression of the target gene. The dsRNA comprises two RNA strands that are sufficiently complementary to hybridize to form a duplex structure. Generally, the duplex structure is between 15 and 30, more generally between 18 and 25, yet more generally between 19 and 24, and most generally between 19 and 21 base pairs in length. In certain embodiments, longer dsRNAs of between 25 and 30 base pairs in length are typical. Similarly, the region of complementarity to the target sequence is between 15 and 30, more generally between 18 and 25, yet more generally between 19 and 24, and most generally between 19 and 21 nucleotides in length. In some embodiments, the dsRNA is between 10 and 15 nucleotides in length, and in other embodiments, the dsRNA is between 25 and 30 nucleotides in length. The dsRNA featured herein may further comprise one or more single-stranded nucleotide overhang(s). The dsRNA can be synthesized by standard methods known in the art as further discussed below, e.g., by use of an automated DNA synthesizer, such as are commercially available from, for example, Biosearch, Applied Biosystems, Inc. In one embodiment, the target gene is a human target gene.

The skilled person is well aware that dsRNAs having a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, the dsRNAs can include at least one strand of a length of minimally 21 nucleotides. It can be reasonably expected that shorter dsRNAs having a known sequence minus only a few nucleotides on one or both ends may be similarly effective as compared to the dsRNAs of the lengths described above. Hence, dsRNAs having a partial sequence of at least 15, 16, 17, 18, 19, 20, or more contiguous nucleotides, and differing in their ability to inhibit the expression of the target gene in a FACS assay as described herein below by not more than 5, 10, 15, 20, 25, or 30% inhibition from a dsRNA having the full sequence, are contemplated by the invention. Further, dsRNAs that cleave within the target sequence can readily be made using the target gene sequence and the target sequence provided.

DsRNAs that target within the sequence targeted by a first dsRNA are suitable for use in the featured compositions and methods. As used herein, a second dsRNA targets within the sequence of a first dsRNA if the second dsRNA cleaves the message anywhere within the mRNA that is complementary to the antisense strand of the first dsRNA. Such a second dsRNA will generally consist of at least 15 contiguous nucleotides coupled to additional nucleotide sequences taken from the region contiguous to the selected sequence in the target gene.

The dsRNA featured herein can contain one or more mismatches to the target sequence. In one embodiment, the dsRNA contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotides from either the 5' or 3' end of the region of complementarity. For example, for a 23 nucleotide dsRNA strand which is complementary to a region of the target gene, the dsRNA generally does not contain any mismatch within the central 13 nucleotides. The methods described within the invention can be used to determine whether a dsRNA containing a mismatch to a target sequence is effective in inhibiting the expression of the target gene. Consideration of the efficacy of dsRNAs with mismatches in inhibiting expression of the target gene is important, especially if the particular region of complementarity in the target gene is known to have polymorphic sequence variation within the population.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. In one embodiment, the antisense strand of the dsRNA has a 1 to 10 nucleotide overhang at the 3' end and/or the 5' end. In one embodiment, the sense strand of the dsRNA has a 1 to 10 nucleotide overhang at the 3' end and/or the 5' end. In another embodiment, one or more of the nucleotides in the overhang is replaced with a nucleoside thiophosphate.

In yet another embodiment, the dsRNA is chemically modified to enhance stability. For example, the nucleic acids may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Specific examples of dsRNA compounds useful for the applications described herein include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Typical modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is herein incorporated by reference.

Typical modified dsRNA backbones that do not include a phosphorus atom therein have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, a dsRNA mimetic that has been shown to have excellent hybridization properties, is referred to as a peptide nucleic acid (PNA). In PNA compounds, the sugar backbone of a dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Many embodiments featured herein include dsRNAs with phosphorothioate backbones and oligonucleosides with heteroatom backbones, and in particular —$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. DsRNAs having morpholino backbone structures of the above-referenced U.S. Pat. No. 5,034,506 are also useful for the applications described herein.

Modified dsRNAs may also contain one or more substituted sugar moieties. Typical dsRNAs include, for example, one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly exemplifications include O[($CH_2$)$_n$O]$_m CH_3$, O($CH_2$)$_n OCH_3$, O($CH_2$)$_n NH_2$, O($CH_2$)$_n CH_3$, O($CH_2$)$_n ONH_2$, and O($CH_2$)$_n ON[(CH_2)_n CH_3]_2$, where n and m are from 1 to about 10. Other exemplary dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of a dsRNA, or a group for improving the pharmacodynamic properties of a dsRNA, and other substituents having similar properties. A typical modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxy-alkoxy group. Other typical modifications include 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

Other exemplary modifications include 2'-methoxy (2'-$OCH_3$), 2'-aminopropoxy (2'-$OCH_2CH_2CH_2NH_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

DsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds featured herein. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., DsRNA Research and Applications, CRC Press, Boca Raton, 1993, pp. 276-278) and are typical base substitutions, particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, each of which is herein incorporated by reference, and U.S. Pat. No. 5,750,692, also herein incorporated by reference.

Another typical modification of dsRNAs involves chemically linking to the dsRNA one or more moieties or conjugates which enhance the activity, cellular distribution or cellular uptake of the dsRNA. Such moieties include but are not limited to lipid moieties such as a cholesterol moiety (Letsinger et al., Proc. Natl. Acid. Sci. USA, 199, 86, 6553-6556), cholic acid (Manoharan et al., Biorg. Med. Chem. Let., 1994 4 1053-1060), a thioether, e.g., beryl-S-tritylthiol (Manoharan et al., Ann. N.Y. Acad. Sci., 1992, 660, 306-309; Manoharan et al., Biorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Representative U.S. patents that teach the preparation of such dsRNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within a dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of a dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxydsRNAs hybridizing to the same target region. Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate.

In some embodiments, an oligonucleotide described herein is covalently bound to a lipophilic ligand. Exemplary lipophilic ligands include cholesterol; bile acids; and fatty acids (e.g., lithocholic-oleyl acid, lauroyl acid, docosnyl acid, stearoyl acid, palmitoyl acid, myristoyl acid, oleoyl acid, or linoleoyl acid). The lipophilic ligand can be bound to the oligonucleotide directly or indirectly, for example, via a tether such as a tether that includes a cleavable linking group. In some embodiments, the lipophilic ligand is bound to the oligonucleotide via a position on the oligonucleotide wherein a ribose of the oligonucleotide has been replaced, for example, by a monomer such as a pyrrolidine monomer.

Exemplary oligonucleotides covalently bound to a lipophilic moiety include the following structure of formula (I), incorporated into the oligonucleotide (e.g., an oligonucleotide described herein):

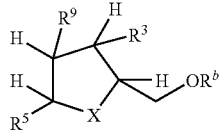

(I)

wherein:
X is N(CO)R$^7$, or NR$^7$;
each of R$^3$, R$^5$ and R$^9$, is, independently, H, OH, OR$^a$, OR$^b$ provided that only one of R$^3$, R$^5$, or R$^9$ is OH, OR$^a$, or OR$^b$;
R$^7$ is C$_1$-C$_{20}$ alkyl substituted with NR$^c$R$^d$ or NHC(O)R$^d$;
R$^a$ is:

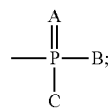

R$^b$ is

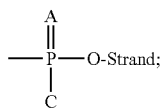

each of A and C is, independently, O or S;
B is OH, O$^-$, or

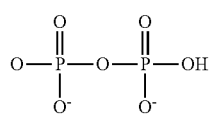

R$^c$ is H or C$_1$-C$_6$ alkyl; and
R$^d$ is a lipophilic ligand, including, for example, cholesterol; a bile acid; or a fatty acid (e.g., lithocholic-oleyl acid, lauroyl acid, docosnyl acid, stearoyl acid, palmitoyl acid, myristoyl acid, oleoyl acid, or linoleoyl acid). The lipophilic ligand, in some embodiments, can be further tethered to a carbohydrate radical. Other exemplary monomers, which can be incorporated into an oligonucleotide described herein and covalently bound to a lipophilic moiety are described, for example, in US 2005/0107325, which is incorporated by reference herein in its entirety.

IIb. Single-Stranded Oligonucleotides

Single stranded oligonucleotides, including those described and/or identified as microRNAs or mirs which may be used as targets or may serve as a template for the design of oligonucleotides featured herein are taught, for example, in Esau, et al. U.S. Publication 20050261218 (U.S. Ser. No. 10/909,125) entitled "Oligomeric compounds and compositions for use in modulation small non-coding RNAs" the entire contents of which are incorporated herein by reference. It will be appreciated by one of skill in the art that any chemical modifications or variations which apply to the double stranded oligonucleotides described above, also apply to single stranded oligonucleotides. As such, the description has not been repeated here.

III. Formulated Lipid Particles (FLiPs)

A FLiP includes (a) at least one of a single or double stranded oligonucleotide, where the oligonucleotide has been conjugated to a lipophile, and (b) at least one of an emulsion or liposome to which the conjugated oligonucleotide has been aggregated, admixed or associated.

It is known that covalent conjugation of highly hydrophobic cholesterol to RNAs mediates cellular import of double-stranded RNAs and single-stranded antisense RNAs and elicits RNA interference and microRNA silencing, respectively. It has also been shown that cholesterol-conjugated RNAs bind to HDL and LDL lipoprotein particles which mediate cellular uptake upon binding to their respective receptors. Both high-density lipoproteins (HDL) and low density lipoproteins (LDL) play a critical role in cholesterol transport. HDL directs siRNA delivery into liver, gut, kidney and steroidogenic organs, whereas LDL targets siRNA primarily to liver (Wolfrum et al. Nature Biotechnology Vol. 25 (2007)). However, up to day, no method for muscle-specific delivery of lipid-conjugated RNAs exists. The technical problem to be solved is to provide a non-toxic carrier for oligonucleotides that is targeting the oligonucleotides specifically to heart, lung and muscle tissues. The problem is solved by the use of the formulated lipid particles (FliPs).

Liposomes are, due to their unique properties, another widely used tool for transporting drugs (V. P. Torchilin, Nature Rev. Drug Discov. 2005, 4(2):145-160). A liposome is a spherical, self-closed structure formed by one or several concentric lipid bilayers with an aqueous phase inside and between lipid bilayers. Liposomes can vary in size, shape and composition. Traditionally, liposomes refer to a membrane composed of a phospholipid and cholesterol bilayer. Liposomes can be composed of naturally-derived phospholipids with mixed lipid chains like egg phosphatidylethanolamine, or of pure surfactant components like dioleoylphosphatidylethanolamine. A liposome encapsulates a region on aqueous solution inside a hydrophobic membrane; dissolved hydrophilic solutes cannot readily pass through the lipids. Hydrophobic chemicals can be dissolved into the membrane, and in this way, liposomes can carry both hydrophobic molecules and hydrophilic molecules. To deliver the molecules to sites of action, the lipid bilayer can fuse with other bilayers such as the cell membrane, thus delivering the liposome contents.

Immunoliposomes have been designed for accumulation in desired tissues and organs. The use of targeted liposomes with surface-attached ligands capable of recognizing and binding to cells of interest has been suggested. Folate and transferrin mediates liposome targeting to tumor cells. Targeting tumors with folate- or transferrin-modified liposomes represents a promising approach, since folate and transferrin receptors are frequently over expressed in tumor cells.

Another source for liposomes is Intralipid®. Intralipid® is a brand name for the first safe fat emulsion for human use, approved in 1962 and invented by Professor Arvid Wretlind, Sweden. It is given intravenously to patients who are unable to get enough fat in their diet. It is therefore completely non-toxic and well tolerated in human.

Intralipid® 20% (a 20% intravenous fat emulsion) is a sterile, non-pyrogenic fat emulsion prepared for intravenous administration as a source of calories and essential fatty acids. It is made up of 20% soybean oil, 1.2% egg yolk phospholipids, 2.25% glycerin, and water for injection. In addition, sodium hydroxide has been added to adjust the pH so that the final product pH is about 8, ranging from 6 to 8.9. Intralipid® 20% has an osmolality of approximately 350 mosmol/kg water (which represents 260 mosmol/liter of emulsion) and contains emulsified fat particles of approximately 0.5 micron size. The soybean oil is a refined natural product consisting of a mixture of neutral triglycerides of predominantly unsaturated fatty acids.

The major component fatty acids are linoleic acid, $C_{18}H_{32}O_2$ (44-62%); oleic acid, $C_{18}H_{34}O_2$ (19-30%); palmitic acid, $C_{16}H_{32}O_2$ (7-14%); linolenic acid, $C_{18}H_{30}O_2$ (4-11%) and stearic acid, $C_{18}H_{36}O_2$ (1.4-5.5%). Soybean oil additionally contains traces of lauric acid, myristic acid, arachidic acid and palmitioleic acid.

Purified egg phosphatides are a mixture of naturally occurring phospholipids which are isolated from the egg yolk. These phospholipids contain saturated and unsaturated fatty acids and either the choline or ethanolamine ester of phosphoric acid. Glycerol is chemically designated $C_3H_8O_3$ and is a clear colorless, hygroscopic syrupy liquid.

Many liposomes are toxic, in part because of stimulating inflammatory cytokine release, and their application is therefore limited for medical use as drug delivery system. Intralipid® is nontoxic and approved for medical application.

In some embodiments, another suitable oil, such as safflower oil, may serve to produce the liposome or emulsion component of the FLiP.

Analysis of Intralipid® by FPLC revealed that this emulsion contains various stable lipid particles of distinct size (FIG. 1). One specific fraction was shown by the present inventors to have an affinity to heart, lung and muscle tissues. This specific fraction is called Intralipid® #1. The lipid composition of Intralipid® #1 is similar to the complete Intralipid® mixture but contains one or several specific lipid-binding proteins of MW between 15 and 35 kD.

While the present exemplars teach a FLiP having a liposome, FLiP compositions may also include an emulsion component, or will include an emulsion instead of a liposome. The liposome of a FLiP may include triacylglycerol, phospholipids, glycerol and one or several lipid-binding proteins aggregated, admixed or associated via a lipophilic linker molecule with a single- or double-stranded oligonucleotide, where the liposome has an affinity to heart, lung and/or muscle tissue. Surprisingly, it has been found that due to the one or several lipid-binding proteins in combination with the above mentioned lipids, the affinity to heart, lung and/or muscle tissue is very specific. These liposomes may therefore serve as carriers for oligonucleotides. Due to their affinity to heart, lung and muscle cells, they may specifically transport the oligonucleotides to these tissues. Therefore, liposome aggregates may be used for many severe heart, lung and muscle diseases, such as myocarditis, ischemic heart disease, myopathies, cardiomyopathies, metabolic diseases, soft tissue diseases and sarcomas, muscular dystrophy, muscle sprains and strains, interstitial lung disease (pulmonary fibrosis) and rhabdomyosarcomas.

In one embodiment, a FLiP includes a liposome having about 15-25% triacylglycerol, about 0.5-2% phospholipids, about 1-3% glycerol, and one or several lipid-binding proteins.

In another embodiment, a FLiP includes a liposome having about 15-25% triacylglycerol, about 1-2% phospholipids, about 2-3% glycerol, and one or several lipid-binding proteins.

In yet another embodiment, a FLiP includes a liposome having about 20% triacylglycerol, about 1.2% phospholipids and about 2.25% glycerol, which corresponds to the total composition of Intralipid®, and one or several lipid-binding proteins.

In another embodiment, the liposome component is the fraction herein known as Intralipid® #1. In another embodiment and alternatively, the emulsion component of the FLiP is Intralipid® #1.

In one embodiment, the FLiP has a particle size of about 20-50 nm or about 30-50 nm, e.g., about 35 nm or about 40 nm.

In another embodiment, the FLiP has a particle size of at least about 100 nm. FLiPs may alternatively be between about 100-150 nm, e.g., about 110 nm, about 120 nm, about 130 nm, or about 140 nm, whether characterized as liposome- or emulsion-based.

In another embodiment, multiple FLiPs are aggregated together. In this embodiment, it is envisioned that multiple FLiPs are delivered, and hence the size may be larger than 100 nm.

The stoichiometry of oligonucleotide to emulsion or liposome may be 1:1. Alternatively, the stoichiometry may be 1:many, many:1 or many:many, where many is greater than 2.

In another embodiment, the oligonucleotide component of the FLiP is aggregated, associated or admixed with the liposome or emulsion component via a lipophilic moiety. This aggregation, association or admixture may be at the surface of the liposome or emulsion. Alternatively, some integration of any of a portion or all of the lipophilic moiety may occur, extending into the liposome or emulsion. Any lipophilic linker molecule that is able to bind oligonucleotides to lipids can be chosen. Examples include cholesterol, pyrrolidine and hydroxyprolinol.

The oligonucleotide component of a FLiP is, for example, an RNA, an oligonucleotide mediating RNA interference (e.g., a dsRNA), an oligonucleotide targeting RNAs, or an oligonucleotide targeting proteins.

The invention further relates to selecting the liposomes or emulsion component from an Intralipid® emulsion. It is noted that the source of the lipid components, particularly the soybean or safflower oil may alter the fractionation pattern and or efficacy of the delivery or silencing. It is within the skill of one in the art, following the methods described herein, to perform comparative studies in selecting the most optimized fractions based on the commercial sources of the components. One embodiment provides a method of optimizing the lipid component of the FLiP whereby commercial sources of oils or other components are compared.

Any method fractionating the Intralipid® emulsion and separating the different lipid particles can be chosen. Liposome particles of 20-50 nm, e.g., 30-50 nm, such as about 35 nm or about 40 nm in size may be selected. Emulsion particles of 100-150 nm, e.g., around 100 nm, in size may be selected.

Exemplary fractionating methods include chromatography, e.g., liquid chromatography and ultracentrifugation.

The process for making the liposomes includes the steps of:
a) mixing a lipid emulsion with one or several single- or double-stranded lipophile (e.g. cholesterol) conjugated oligonucleotides that may be chemically modified;
b) fractionating this mixture; and
c) selecting the fraction with particles of 30-50 nm, such as about 40 nm in size.

As shown in the present examples, cholesterol-conjugated RNAs (Chol-apoB1 and Antagomir-16) bind to Intralipid® peak #1 that elutes between fraction 40 to 50 by FPLC and contains particles between 30 and 50 nm in size.

Alternatively, the liposomes can be made by first isolating the lipid particles comprising triacylglycerol, phospholipids, glycerol and one or several lipid-binding proteins and corresponding to Intralipid® #1 particles and then mixing the isolated particles with >2-fold molar excess of single- or double-stranded lipophile (e.g. cholesterol) conjugated oligonucleotide. The steps of fractionating and selecting the particles are deleted by this alternative process for making the liposomes.

In one embodiment, liposome FLiP aggregates are used as medicaments, such as to treat heart, lung or muscle diseases. Such medicaments are typically used to treat disorders caused by overexpression of particular genes, RNAs or proteins.

In some embodiments, the liposome or emulsion aggregate is contained in a lyophilisat.

In one aspect, a method is provided for selectively targeting a single- or double-stranded oligonucleotide to mammalian heart, lung and/or muscle tissue by contacting a mammal with the oligonucleotide, where the oligonucleotide has been formulated via a lipid emulsion fractionation process according to the description above. It is within the skill of one in the art to identify genes that are selectively or exclusively expressed in particular tissues such as heart, lung or muscle. Any of these genes would serve as a target against which to design single or double stranded oligonucleotides which may then be conjugated to a lipophile and formulated in a FLiP.

Yet another aspect relates to a method for reducing expression of a gene in mammalian tissue in vivo by contacting the tissue with a FLiP (such as either a liposome or emulsion containing FLiP, or both).

IV. Pharmaceutical Compositions Comprising Formulated Oligonucleotides

In one embodiment, the invention provides pharmaceutical compositions containing an oligonucleotide as described herein and a pharmaceutically acceptable carrier. Such compositions are useful for treating diseases or disorders associated with the expression or activity of the target gene, such as pathological processes mediated by target gene expression.

The pharmaceutical compositions featured herein are administered in dosages sufficient to inhibit expression of the target gene. In general, a suitable dose of total oligonucleotide will be in the range of 0.01 to 200.0 milligrams per kilogram body weight of the recipient per day, generally in the range of 0.02 to 50 mg per kilogram body weight per day. For example, the dsRNA can be administered at 0.01 mg/kg, 0.1, mg/kg, 0.05 mg/kg, 0.5 mg/kg, 1 mg/kg, 2 mg/kg, 3 mg/kg, 10 mg/kg, 20 mg/kg, 30 mg/kg, 40 mg/kg, or 50 mg/kg per single dose. The pharmaceutical composition may be administered once daily or may be administered as two, three, or more sub-doses at appropriate intervals throughout the day or even using continuous infusion or delivery through a controlled release formulation. In that case, the oligonucleotide contained in each sub-dose must be correspondingly smaller in order to achieve the total daily dosage. The dosage unit can also be compounded for delivery over several days, e.g., using a conventional sustained release formulation which provides sustained release of the oligonucleotide over a several day period. Sustained release formulations are well known in the art and are particularly useful for delivery of agents at a particular site, such as could be used with the agents featured herein. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual oligonucleotides encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by target gene expression. Such models are used for in vivo testing of oligonucleotide, as well as for determining a therapeutically effective dose.

The pharmaceutical compositions featured herein may be administered in a number of ways depending upon whether local or systemic treatment is desired and upon the area to be treated. Administration may be topical (e.g., by a transdermal patch), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable formulations include those in which the FLiPs are in admixture with a topical delivery agent such as lipids, liposomes, fatty acids, fatty acid esters, steroids, chelating agents and surfactants.

Suitable lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). FLiPs may themselves be encapsulated within liposomes or may form complexes thereto, in particular to cationic liposomes. Alternatively, FLiPs may be complexed to lipids, in particular to cationic lipids. Suitable fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof.

Compositions for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Typical oral formulations are those in which FLiPs are administered in conjunction with one or more penetration enhancers surfactants and chelators. Typical surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Typical fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Combinations of penetration enhancers are also suitable and include, for example, fatty acids/salts in combination with bile acids/salts. One typical combination is the sodium salt of lauric acid, capric acid and UDCA. Further penetration enhancers include polyoxyethylene-9-lauryl ether, polyoxyethylene-20-cetyl ether. DsRNAs featured herein may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Typical complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly (ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. application. Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999), each of which is incorporated herein by reference in their entirety.

Additional compositions useful for parenteral, intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions featured herein include, but are not limited to, solutions, emulsions, and liposome-containing formulations. These compositions may be generated from a variety of components that include, but are not limited to, preformed liquids, self-emulsifying solids and self-emulsifying semisolids. Particularly preferred are formulations that target the lung, heart and other muscles.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions may be formulated into any of many possible dosage forms such as, but not limited to, tablets, capsules, gel capsules, liquid syrups, soft gels, suppositories, and enemas. The compositions may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Emulsions

FLiP compositions may be prepared and formulated as emulsions. Emulsions are typically heterogenous systems of one liquid dispersed in another in the form of droplets (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories:

synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment, the compositions of FLiPs are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex® 300, Captex® 355, Capmul® MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations will facilitate the increased systemic absorption of dsRNAs and nucleic acids from the gastrointestinal tract, as well as improve the local cellular uptake of dsRNAs and nucleic acids.

Microemulsions may also contain additional components and additives such as sorbitan monostearate (Grill 3), Labrasol®, and penetration enhancers to improve the properties of the formulation and to enhance the absorption of dsRNAs and single-stranded nucleic acids. Penetration enhancers used in the microemulsions may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Liposomes

As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/po-lyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes of the FLiPs also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{12}15G$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556, 948 (Tagawa et al.) describe PEG-containing liposomes that can be further derivatized with functional moieties on their surfaces.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Penetration Enhancers

In some embodiments, the FLiPs employ penetration enhancers to effect the efficient delivery of nucleic acids, particularly dsRNAs, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Carriers

Certain compositions of FLiPs may also incorporate carrier compounds in the formulation. As used herein, "carrier compound" or "carrier" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration that do not deleteriously react with nucleic acids can also be used to formulate the compositions. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

FLiP compositions may additionally contain other adjunct components conventionally found in pharmaceutical compositions at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the FLiP compositions, such as dyes, flavoring agents, preservatives, antioxidants, opacifiers, thickening agents and stabilizers. However, such materials, when added, should not unduly interfere with the biological activities of the components of the compositions. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

In some embodiments, pharmaceutical compositions contain (a) one or more oligonucleotide compounds and (b) one or more other chemotherapeutic agents that function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206-1228, Berkow et al., eds., Rahway, N.J. When used with the compounds featured herein, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions featured herein. See, generally, The Merck Manual of Diagnosis and Therapy, 15th Ed., Berkow et al., eds., 1987, Rahway, N.J., pages 2499-2506 and 46-49, respectively). Other non-antisense chemotherapeutic agents are also within the scope of the featured invention. Two or more combined compounds may be used together or sequentially.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are typical.

The data obtained from cell culture assays and animal studies can be used in formulation a range of dosage for use in humans. Suitable dosages lie generally within a range of circulating concentrations that include the ED50 with little or no toxicity. The dosage may vary within this range depending upon the dosage form employed and the route of administration utilized. For the compounds featured herein, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs featured herein can be administered in combination with other known agents effective in treatment of pathological processes mediated by target gene expression. In any event, the administering physician can adjust the amount and timing of oligonucleotide administration on the basis of results observed using standard measures of efficacy known in the art or described herein.

V. Methods for Treating Diseases Caused by Expression of a Target Gene Using the Formulated FLiP compositions The invention relates in particular to FLiP compositions having (a) at least one of a single or double stranded oligonucleotide, where the oligonucleotide has been conjugated to a lipophile, and (b) at least one of an emulsion or liposome to which the conjugated oligonucleotide has been aggregated, admixed or associated for the treatment of a disease or disorder or condition of the heart, lung or muscle.

The invention furthermore relates to the use of a FLiP or a pharmaceutical composition thereof, e.g., for treating cancer or for preventing tumor metastasis, e.g., a soft tissue sarcoma, such as rhabdomyosarcoma, in combination with other pharmaceuticals and/or other therapeutic methods, e.g., with known pharmaceuticals and/or known therapeutic methods, such as, for example, those which are currently employed for treating cancer and/or for preventing tumor metastasis. Preference is given to a combination with radiation therapy and chemotherapeutic agents, such as cisplatin, cyclophosphamide, 5-fluorouracil, adriamycin, daunorubicin or tamoxifen.

The invention can also be practiced by including with a specific oligonucleotide, in combination with another anticancer chemotherapeutic agent, such as any conventional chemotherapeutic agent. The combination of a specific binding agent with such other agents can potentiate the chemotherapeutic protocol. Chemotherapeutic protocols known in the art are suitable for use with the methods featured herein. Any chemotherapeutic agent can be used, including alkylating agents, antimetabolites, hormones and antagonists, radioisotopes, as well as natural products. For example, a compound featured herein can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of a tetracycline compound with another treatment modality, e.g., surgery, radiation, etc., also referred to herein as "adjunct antineoplastic modalities." Thus, the methods featured herein can be employed with such conventional regimens with the benefit of reducing side effects and enhancing efficacy.

Compositions containing FLiPs are also useful for targeting diseases and disorders of the lung, such as interstitial lung disease (ILD) (pulmonary fibrosis). Diseases and disorders affecting the heart, such as cardiomyopathy and heart disease can also be treated by FLiP compositions. Other muscle diseases and disorders suitable for treatment with compositions formulated with FLiPs include, for example, muscular dystrophy, sprains and strains, and other myopathies.

VI. Methods for Inhibiting Expression of the Target Gene Using FLiP Formulated Oligonucleotides The invention provides methods for inhibiting the expression of the target gene in a mammal, such as by administering a FLiP composition to the mammal, such that expression of the target gene is silenced.

In one embodiment, a method for inhibiting target gene expression includes administering a composition containing a nucleotide sequence that is complementary to at least a part of an RNA transcript of the target gene and the other having a nucleotide sequence that is complementary to at least a part of an RNA transcript of the gene of the mammal to be treated. When the organism to be treated is a mammal such as a human, the composition may be administered by any means known in the art including, but not limited to oral or parenteral routes, including intravenous, intramuscular, subcutaneous, transdermal, airway (aerosol), nasal, rectal, and topical (including buccal and sublingual) administration. In some embodiments, the compositions are administered by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Oligonucleotide Synthesis

Source of Reagents

Where the source of a reagent is not specifically given herein, such reagent may be obtained from any supplier of reagents for molecular biology at a quality/purity standard for application in molecular biology.

siRNA (dsRNA) Synthesis

Single-stranded RNAs were produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol-3'), an appropriately modified solid support was used for RNA synthesis. The modified solid support was prepared as follows:

Diethyl-2-azabutane-1,4-dicarboxylate AA

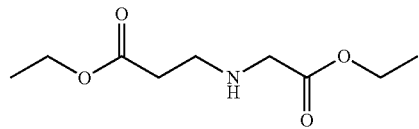

A 4.7 M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until completion of the reaction was ascertained by TLC. After 19 h the solution was partitioned with dichloromethane (3×100 mL). The organic layer was dried with anhydrous sodium sulfate, filtered and evaporated. The residue was distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

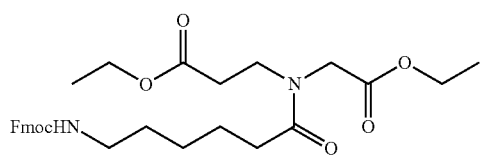

Fmoc-6-amino-hexanoic acid (9.12 g, 25.83 mmol) was dissolved in dichloromethane (50 mL) and cooled with ice. Diisopropylcarbodiimde (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. Completion of the reaction was ascertained by TLC. The reaction mixture was concentrated under vacuum and ethyl acetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

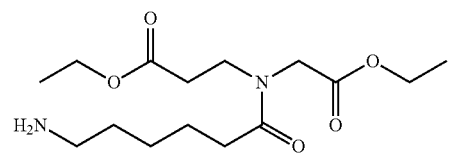

3-{Ethoxycarbonylmethyl-[6-(9H-fluoren-9-ylmethoxy-carbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated under vacuum, water was added to the residue, and the product was extracted with ethyl acetate. The crude product was purified by conversion into its hydrochloride salt.

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD

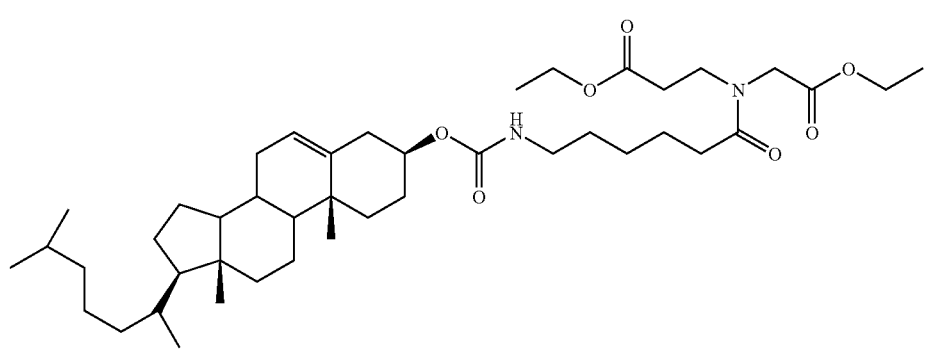

The hydrochloride salt of 3-[(6-Amino-hexanoyl)-ethoxy-carbonylmethyl-amino]-propionic acid ethyl ester AC (4.7 g, 14.8 mmol) was taken up in dichloromethane. The suspension was cooled to 0° C. on ice. To the suspension diisopropyl-ethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (10.3 g, 92%).

1-{6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}-4-oxo-pyrrolidine-3-carboxylic acid ethyl ester AE

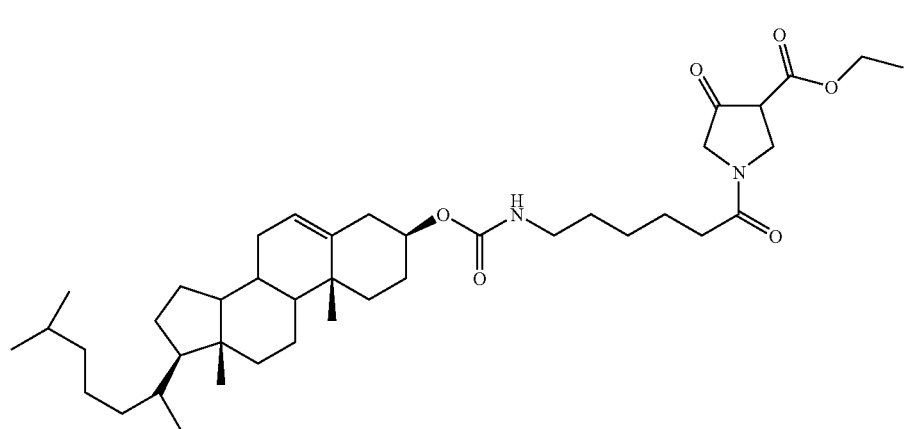

Potassium t-butoxide (1.1 g, 9.8 mmol) was slurried in 30 mL of dry toluene. The mixture was cooled to 0° C. on ice and 5 g (6.6 mmol) of diester AD was added slowly with stirring within 20 mins. The temperature was kept below 5° C. during the addition. The stirring was continued for 30 mins at 0° C. and 1 mL of glacial acetic acid was added, immediately followed by 4 g of NaH$_2$PO$_4$.H$_2$O in 40 mL of water The resultant mixture was extracted twice with 100 mL of dichloromethane each and the combined organic extracts were washed twice with 10 mL of phosphate buffer each, dried, and evaporated to dryness. The residue was dissolved in 60 mL of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to dryness. The residue was purified by column chromatography using 25% ethylacetate/hexane to afford 1.9 g of b-ketoester (39%).

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

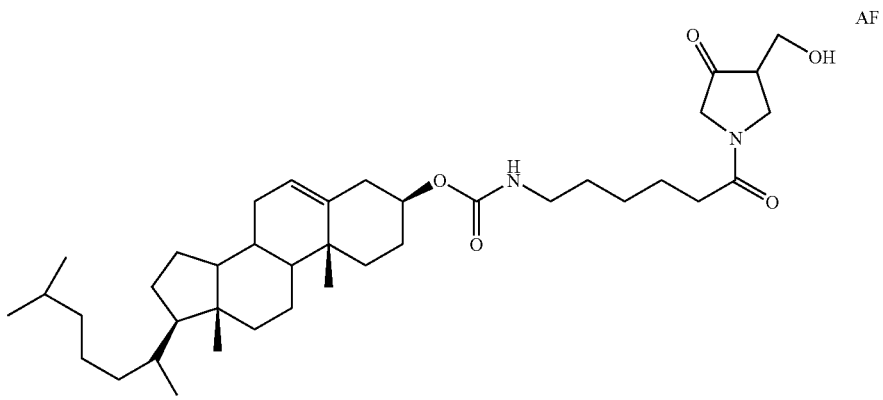

Methanol (2 mL) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h. After cooling to room temperature, 1 N HCl (12.5 mL) was added, the mixture was extracted with ethylacetate (3×40 mL). The combined ethylacetate layer was dried over anhydrous sodium sulfate and concentrated under vacuum to yield the product which was purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

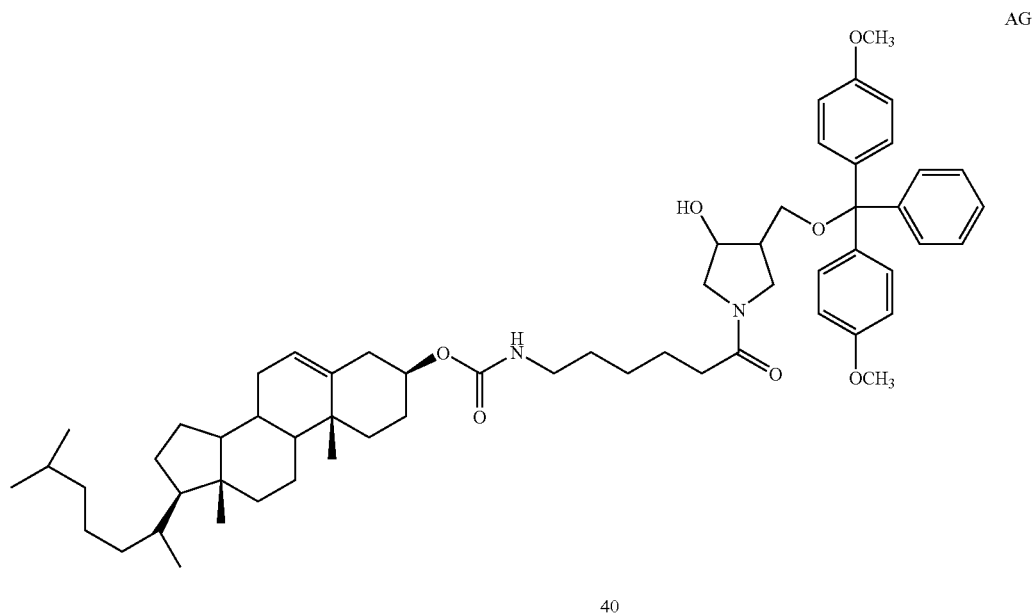

AG

Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature overnight. The reaction was quenched by the addition of methanol. The reaction mixture was concentrated under vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, Rf=0.5 in 5% MeOH/CHCl$_3$) (1.75 g, 95%).

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH

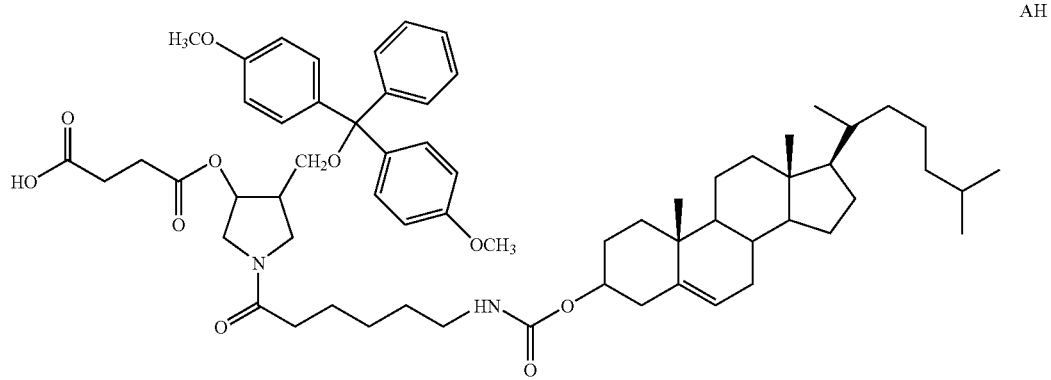

AH

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.

Cholesterol Derivatised CPG AI

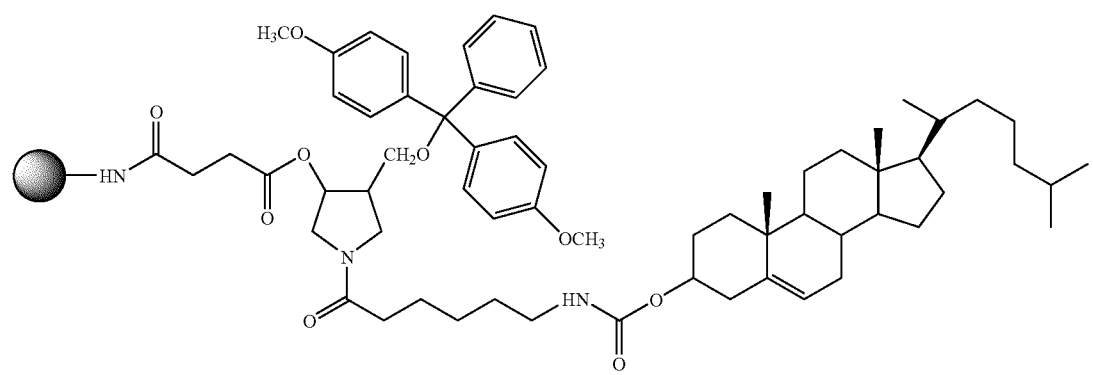

AI

Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using a wrist-action shaker (5 mins). Long chain alkyl amine-CPG (LCAA-CPG) (1.5 g, 61 mM) was added. The suspension was agitated for 2 h. The CPG was filtered through a sintered funnel and washed with acetonitrile, dichloromethane and ether successively. Unreacted amino groups were masked using acetic anhydride/pyridine. The achieved loading of the CPG was measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") was performed as described in WO 2004/065601, except that, for the cholesteryl derivative, the oxidation step was performed using the Beaucage reagent in order to introduce a phosphorothioate linkage at the 5'-end of the nucleic acid oligomer.

Nucleic acid sequences are represented using standard nomenclature, and specifically the abbreviations of Table 1.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | adenosine |
| C | cytidine |
| G | guanosine |

TABLE 1-continued

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| T | thymidine |
| U | uridine |
| N | any nucleotide (G, A, C, U or T) |
| a | 2'-O-methyladenosine |
| c | 2'-O-methylcytidine |
| g | 2'-O-methylguanosine |
| u | 2'-O-methyluridine |

TABLE 1-continued

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| s | Phosphorothioate linkage |
| dT | 2'-deoxythymidine |

Example 2

Formation of Intralipid® Complexes with Cholesterol-Conjugated RNA

Intralipid® (Sigma 20%) concentration is 200 mg/ml (approx. 570 μM). Intralipid® is diluted to 133 μM and incubated 1:2 with Chol-conjugated RNA (Chol-RNA) (4 mg/ml, 266 μM, spiked with a small amount of $^{32}$P labeled Chol-RNA for quantification) for 30 minutes at room temperature. Unbound Chol-RNA is separated by gel filtration using two Suprose 6 column (volume of run: 0.5 ml) (Pharmacia HR 10/30 code #17-0537-01) with FPLC running buffer (0.15 M NaCl, 0.01 M Na$_2$HPO$_4$, 0.1 mM EDTA, pH 7.5). The Intralipid®/chol-RNA fraction is collected (particles between 30 to 50 nm) and Chol-RNA content quantified by scintillation counting.

Example 3

Cholesterol-Conjugated RNAs Fractionate with Intralipid® Peak#1 by FPLC

Chol-apoB1-siRNA, a chemically-modified, lipophile-conjugated siRNA-apoB1, was constituted from the corresponding sense strand: 5'-GUCAUCACACUGAAUAC-CAAU$_s$Hyp-L-3' (SEQ ID NO:1) and antisense strand:

5'-AUUGGUAUUCAGUGUGAUGAC$_s$A$_s$C-3' (SEQ ID NO:2) was obtained as described in Soutschek et al. 2004, Nature 432, 173-8. The cholesterol-conjugated sense strand was synthesized from a hydroxyprolinol-lipophile solid support. Cholesterol was tethered to trans-4-hydroxyprolinol via a 6-aminohexanoate linkage to obtain a hydroxyprolinol-lipophile moiety (Hyp) that was subsequently attached to a functionalized control pore glass to obtain the solid support. The letter 'L' represents the lipophile, lower case letters represent 2'-O-methyl sugar modification and subscript 's' stands for phosphorothioate linkages.

The single stranded oligonucleotide, antagomir-16, consisted of 22 nt length with modifications as specified: 5'-c$_s$g$_s$ccaauauuuacgugcug$_s$c$_s$u$_s$a$_s$-Chol-3' (SEQ ID NO:3).

The single stranded oligonucleotide, antagomir-133a, consisted of 21 nt length with modifications as specified: 5'-a$_s$u$_s$-uugguuccauuuuacc$_s$a$_s$g$_s$c$_s$-Chol-3' (SEQ ID NO:4). The lower case letters represent 2'-O-methyl modified nucleotides; subscript 's' represent phosphorothioate linkage.

Figure 7:
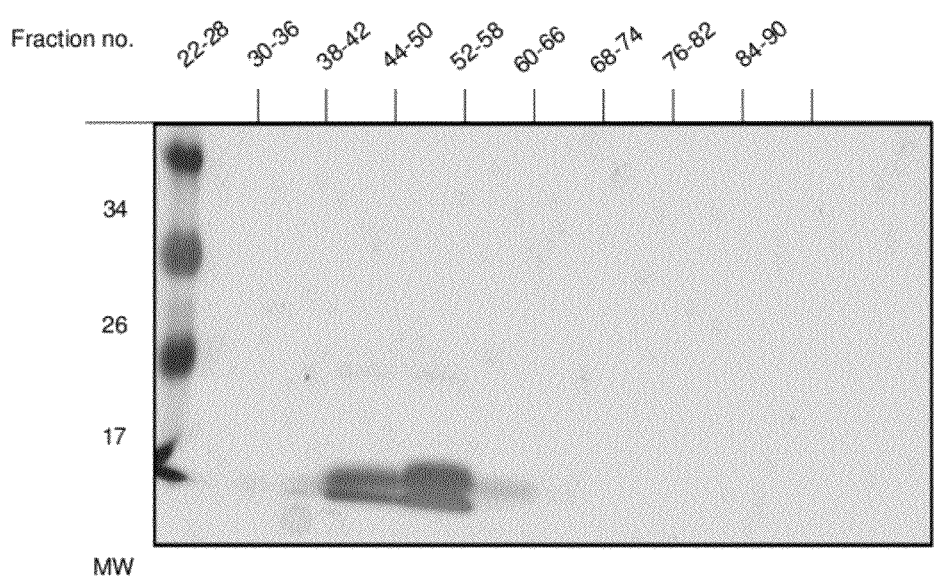
FIG. 7 is a silver-stained polyacrylamide gel showing that low molecular weight proteins are associated with Intralipid® peak#1. Two protein bands at molecular weight (MW) between 10 and 20 kD can be detected in fractions 38-50 (corresponding to the fractions containing Intralipid®#1).

Intralipid® was manufactured by Fresenius Kabi, Uppsala Sweden (100 mL Intralipid® 20% comprising 20 g soybean oil, 1.2 g Phospholipid and 2.25 g glycerol (USP)). FPLC analysis of Intralipid® indicated that the emulsion contains various stable lipid particles of distinct size. Cholesterol-conjugated RNAs (Chol-apoB1-siRNA and antagomir-16) bound with Intralipid® peak#1, which elutes between fractions 40 to 50 (FIG. 1). Intralipid® #1 corresponds to the liposome featured herein. RNAs in FIG. 1 were labeled with $^{32}$P and lipid fractions were determined by UV absorbance at 230 nm (see also FIG. 7).

Example 4

Uptake of Intralipid®/Chol-siRNA is Enriched in Muscle, Heart and Lung

Figure 2:
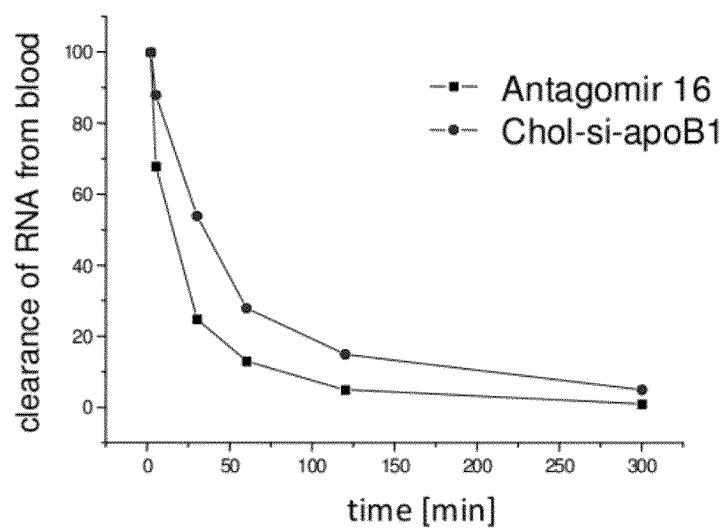
FIG. 2 is a graph depicting plasma clearance of Intralipid®/antagomir-16 and Intralipid®/chol-apoB1-siRNA following tail vein injections.

Plasma clearance of Intralipid®/antagomir-16 and Intralipid®/chol-apoB1-siRNA was examined in mice following tail injections. The blood t1/2 for antagomir-16 was determined to be about 20 minutes, and the blood t1/2 of chol-apoB1-siRNA was determined to be about 40 minutes (FIG. 2). The experiment showed rapid removal of Intralipid®/RNA complexes from the blood after systemic injection.

Figure 3:
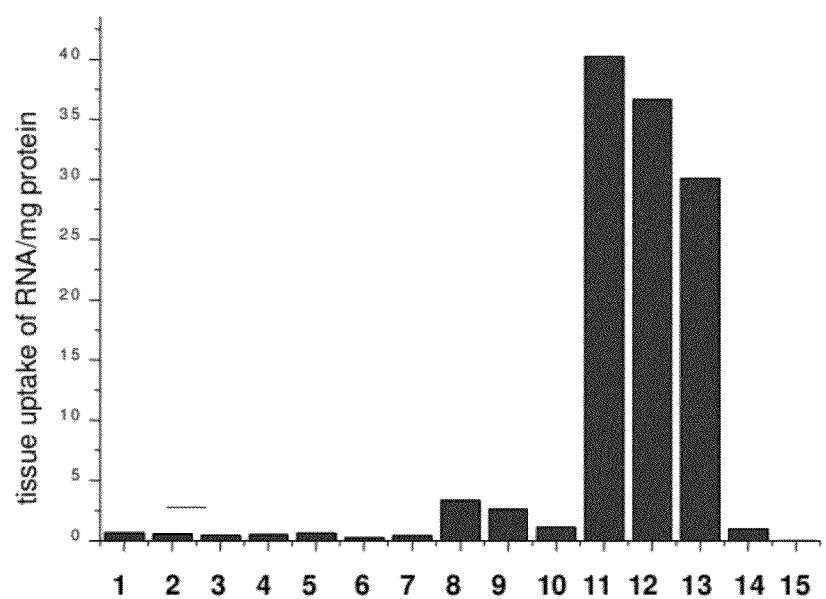
FIG. 3 is a graph depicting tissue uptake of $^{32}$P-labeled chol-apoB1-siRNA mediated by "Intralipid® 1" 4 h after systemic injection. Uptake was normalized per mg protein. Lane 1 represents liver; lane 2 represents stomach; lane 3 represents duodenum; lane 4 represents jejunum; lane 5 represents ilium; lane 6 represents colon; lane 7 represents testis; lane 8 represents kidney; lane 9 represents adrenal; lane 10 represents spleen; lane 11 represents heart; lane 12 represents muscle; lane 13 represents lung; lane 14 represents fat; and lane 15 represents brain.

Tissue uptake of $^{32}$P-labeled chol-apoB1-siRNA mediated by "Intralipid® 1" was measured in mice 4 h after systemic injection. Uptake was normalized/mg protein. The experiment showed selective (enriched) uptake of Intralipid®/chol-siRNA in muscle, heart and lung (FIG. 3).

Figure 4:
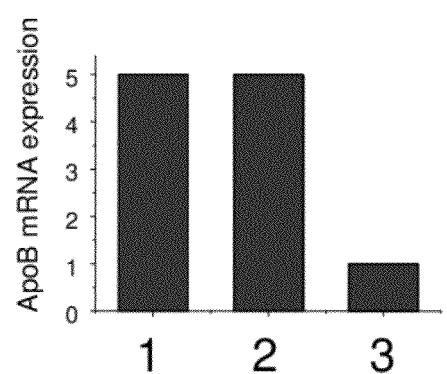
FIG. 4 is a graph depicting ApoB silencing activity of chol-apoB1-siRNA following chol-apoB1-siRNA/Intralipid® 1 injection. Lane 1 represents wildtype (PBS control); lane 2 represents chol-ApoB unconjugated (in the absence of Intralipid® 1); and lane 3 represents chol-ApoB Intralipid® 1 (siRNAs complexed with Intralipid® 1 prior to injection).

ApoB mRNA expression levels in the heart of mice injected with a single injection of chol-apoB1-siRNA at 10 mg/kg bodyweight were measured by real time PCR 24 h after injection. A five-fold decrease of ApoB mRNA compared to control experiments was seen. (FIG. 4).

Example 5

Figure 5:
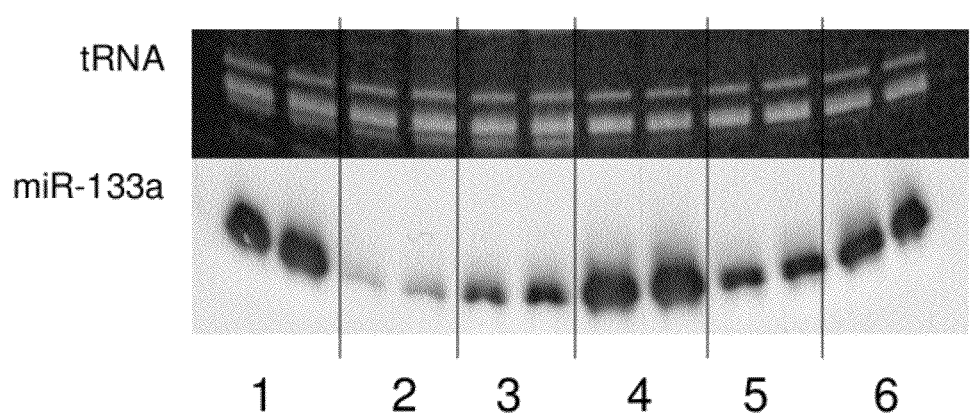
FIG. 5 is a gel depicting silencing of MicroRNA-133a (miR-133a) following antagomir-133a/Intralipid® #1 injection. Expression levels were measured by Northern blotting 24 h after injection. tRNA levels are shown as a loading control. Lanes 1 and 4 represents PBS controls; lanes 2 and 5 represent Intralipid® ant.133a (anagomir-133a that were complexed with Intralipid® 1 prior to injection); lanes 3 and 6 represent ant.133a (injection of antagomir in the absence of Intralipid® 1); lanes 1-3 represents heart tissue; lanes 4-6 represent M. quadriceps.

Injection of Antagomir-133a/Intralipid®#1 in Mice Inhibited Expression of miR-133a in Heart and Quadriceps Intralipid®/miRNA Injection in Mice Mice were injected with a single injection of antagomir-133a/Intralipid® #1 at 50 mg/kg bodyweight. MicroRNA-133a (miR-133a) levels in heart and quadriceps muscle were measured by Northern blotting 24 h after injection. Duplicates were measured for each treatment. The experiment revealed in vivo silencing of miR-133a in heart and quadriceps (FIG. 5).

Example 6

Injection of Antagomir-206/Intralipid®#1 in Mice Inhibited Expression of miR-206 in Quadriceps Mice were injected in duplicates with either PBS (control), antagomir-206, or antagomir-206 that was complexed with Intralipid®#1 at a dose of 3×80 mg/kg body weight (bw) or 3×50 mg/kg, respectively. Mice were sacrificed on day 4 (24 h after the last injection), total RNA was isolated from the quadriceps muscle, and miR-206 levels were analyzed by Northern blotting. tRNA is shown as a loading control.

Figure 6:
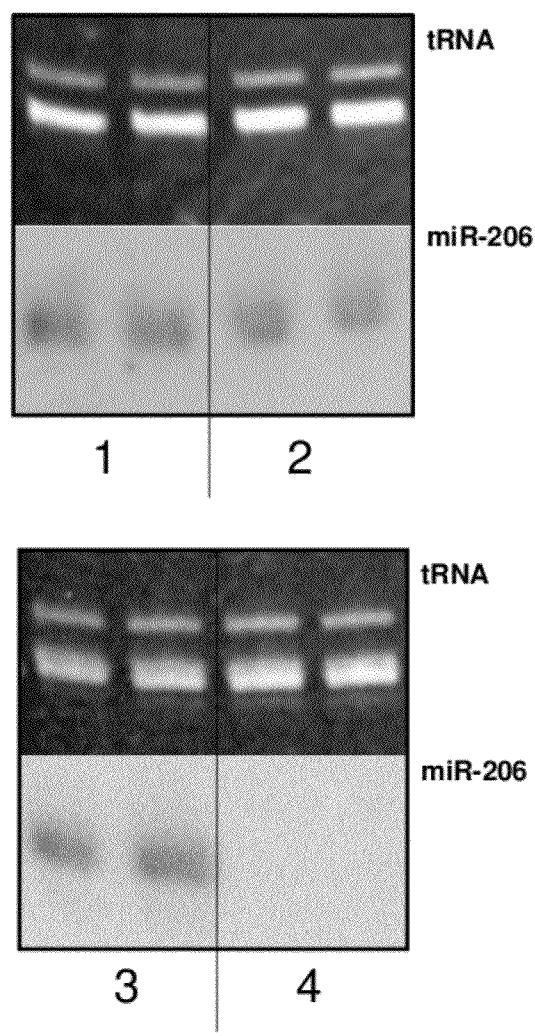
FIG. 6 is a pair of gels depicting the targeting of muscle-specific miR-206 with a lipid-antagomir complex. Lane 1 represents a control sample (3×80 mg/kg bodyweight i.v.); lane 2 represents antagomir-206 (3×80 mg/kg bodyweight i.v.); lane 3 represents a control (3×50 mg/kg bodyweight i.v.) sample; lane 4 represents Intralipid®/antagomir-206 (3×50 mg/kg bodyweight i.v.).

The antagomir-206 used consisted of 22 nt length with modifications as specified: 5'-c$_s$c$_s$acacacuuccuuacauu$_s$c$_s$c$_s$a$_s$-Chol-3' (SEQ ID NO:5). The lower case letters represent 2'-O-methyl modified nucleotides; subscript 's' represent phosphorothioate linkage. The experiment shows complete in vivo silencing of miR-206 following antagomir-206/Intralipid®#1 injection in quadriceps (FIG. 6).

Example 7

Intralipid® 1 Fractionation by HPLC

Intralipid® was fractionated by HPLC. Proteins were extracted from indicated fractions and separated on a 12% polyacrylamide gel. Proteins were visualized by silver staining. Two protein bands at molecular weight (MW) between 10 and 20 kD were detected in fractions 38-50 (corresponding to the fractions containing Intralipid® #1) (FIG. 7) (see also FIG. 1).

Other embodiments are in the claims.

We claim:

1. A formulated lipid particle (FLiP) comprising:
   (a) a double stranded oligonucleotide conjugated to a lipophile, and
   (b) a 20% intravenous fat emulsion to which the lipophile-conjugated double stranded oligonucleotide is associated.

2. The FLiP of claim 1, wherein the double stranded oligonucleotide is a double stranded RNA (dsRNA) comprising at least two strands that are complementary to each other and wherein each of the two strands are at least 15 nucleotides long, and wherein a sense strand comprises a first sequence and an antisense strand comprises a second sequence comprising a region of complementarity which is complementary to at least a part of a target gene, and wherein said region of complementarity is less than 30 nucleotides in length.

3. The FLiP of claim 2, wherein at least one nucleotide of the dsRNA is a modified nucleotide.

4. The FLiP of claim 3, wherein the modified nucleotide is chosen from the group of: a 2'-O-methyl modified nucleotide, a nucleotide comprising a 5'-phosphorothioate group, and a terminal nucleotide linked to a cholesteryl derivative or dodecanoic acid bisdecylamide group.

5. The FLiP of claim 3, wherein said modified nucleotide is chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

6. The FLiP of claim 2, wherein the region of complementarity is between 19 and 21 nucleotides in length.

7. The FLiP of claim 2, wherein the dsRNA comprises a single strand overhang at one or both ends of the dsRNA.

8. The FLiP of claim 2, wherein the sense and antisense strands are each 21 nucleotides in length with 19 base pair complementarity, and wherein the dsRNA has a single strand overhang of 2 nucleotides at the 3' end of each strand.

9. The FLiP of claim 1, wherein the lipophile conjugate is a cholesterol moiety.

10. A method for selectively targeting or delivering a double stranded oligonucleotide comprising two strands to a mammalian tissue comprising contacting a mammal with the FLiP of claim 1.

11. The method of claim 10, wherein said mammalian tissue is heart, lung and/or muscle tissue.

12. The method of claim 10, each strand being 21 nucleotides in length with 19 base pair complementarity and each strand having a single strand overhang of 2 nucleotides at the 3' end.

13. The method of claim 12, wherein the double stranded oligonucleotide is modified with a cholesterol moiety.

14. The method of claim 10, wherein the double stranded oligonucleotide targets ApoB or RhoA.

15. A method of reducing expression of a gene in mammalian tissue comprising contacting said tissue with the FLiP of claim 1 or claim 2 or claim 8.

16. The method of claim 15, wherein said mammalian tissue is heart, lung and/or muscle tissue.

17. The method of claim 15, wherein expression of the gene in the tissue is reduced in vivo in a mammal and said contacting is via systemic delivery to the mammal.

18. A lyophilisat comprising the FLiP of claim 1 or claim 2 or claim 8.

19. The FLiP of claim 1 or claim 2 or claim 8, wherein the oligonucleotide targets ApoB or RhoA.

20. The FLiP of claim 1 or claim 2 or claim 8, wherein the 20% intravenous fat emulsion comprises triacylglycerol, phospholipids, glycerol, and one or several lipid-binding proteins.

21. The FLiP of claim 20, wherein the 20% intravenous fat emulsion comprises 20% triacylglycerol, 1.2% phospholipids, 2.25% glycerol, and one or several lipid-binding proteins.

22. The FLiP of claim 20, wherein the 20% intravenous fat emulsion comprises 20% soybean oil, 1.2% egg yolk phospholipids, 2.25% glycerin, and water.

23. The FLiP of claim 1 or claim 2 or claim 8 having a particle size of 20-50 nm.

24. The FLiP of claim 1 or claim 2 or claim 8 having a particle size of 35 nm.

25. The FLiP of claim 1 or claim 2 or claim 8, wherein the lipophile conjugate comprises cholesterol and the 20% intravenous fat emulsion comprises 20% soybean oil, 1.2% egg yolk phospholipids, 2.25% glycerin, and water, and the particle size is 35 nm.

* * * * *